(12) United States Patent
Fassbender

(10) Patent No.: US 6,391,203 B1
(45) Date of Patent: May 21, 2002

(54) ENHANCED BIOGAS PRODUCTION FROM NITROGEN BEARING FEED STOCKS

(76) Inventor: Alexander G. Fassbender, 3100 George Washington Way, Suite 153, Richland, WA (US) 99352

(*) Notice: Subject to any disclaimer, the term of this patent is extended or adjusted under 35 U.S.C. 154(b) by 0 days.

(21) Appl. No.: 09/721,500

(22) Filed: Nov. 22, 2000

(51) Int. Cl.$^7$ ................................. C02F 3/28
(52) U.S. Cl. ............... 210/603; 210/612; 210/631; 210/903
(58) Field of Search ................. 210/603, 605, 210/630, 631, 903, 612

(56) References Cited

U.S. PATENT DOCUMENTS

| | | |
|---|---|---|
| 3,586,625 A | 6/1971 | Cole et al. |
| 3,871,999 A | 3/1975 | Torpey |
| 3,939,068 A | 2/1976 | Wendt et al. |
| 4,076,515 A * | 2/1978 | Richard ............. 210/603 |
| 4,132,636 A | 1/1979 | Iwase et al. |
| 4,213,857 A | 7/1980 | Ishida et al. |
| 4,315,821 A * | 2/1982 | Climenhuge ............ 210/903 |
| 4,374,730 A | 2/1983 | Braha et al. |
| 4,552,663 A | 11/1985 | Spector et al. |
| 4,816,158 A | 3/1989 | Shimura et al. |
| 4,861,519 A | 8/1989 | Tusa et al. |
| 4,975,194 A | 12/1990 | Fuchs et al. |
| 5,057,220 A | 10/1991 | Harada et al. |
| 5,186,837 A | 2/1993 | Nikolic et al. |
| 5,221,486 A | 6/1993 | Fassbender |
| 5,288,407 A | 2/1994 | Bodwell et al. |
| 5,433,868 A | 7/1995 | Fassbender |
| 5,531,896 A * | 7/1996 | Tambo et al. ............ 210/631 |
| 5,534,148 A | 7/1996 | Suzuki et al. |
| 5,543,051 A * | 8/1996 | Harris ................ 210/903 |
| 5,691,891 A | 11/1997 | Fasullo et al. |
| 5,746,919 A | 5/1998 | Dague et al. |
| 5,776,344 A | 7/1998 | McCarty et al. |
| 5,785,852 A | 7/1998 | Rivard et al. |
| 5,853,588 A | 12/1998 | Molof et al. |
| 5,863,434 A * | 1/1999 | Mussect et al. ............ 210/603 |
| 5,984,992 A | 11/1999 | Greer et al. |

FOREIGN PATENT DOCUMENTS

JP   3-161095   * 7/1991

OTHER PUBLICATIONS

Hansen et al., Anaerobic Digestion of Swine Manure: Inhibition by Ammonia 6/97.

(List continued on next page.)

Primary Examiner—Christopher Upton
(74) Attorney, Agent, or Firm—Mark Rogers; Gary N. Speed

(57) ABSTRACT

A system is disclosed comprising a first anaerobic digester, an ammonia recovery vessel, and a second anaerobic digester. Microorganisms within the first anaerobic digester are primarily hydrolyzers and acetogens, and microorganisms within the second anaerobic digester are primarily methanogens. A nitrogen containing feed stock is passed to the first digester in which the feed stock is treated to accomplish hydrolysis and acetogenesis. An effluent stream from the first digester is passed to the ammonia recovery vessel in which ammonia is removed to generate a low ammonia effluent stream. The low ammonia effluent stream is then passed to the second digester in which it is treated to accomplish methanogenesis, thereby generating a biogas. In an alternate embodiment, a single anaerobic digester is used, an effluent stream is removed from the reactor, treated for ammonia removal, and recycled to the digester at a rate sufficient to keep ammonia levels within the digester sufficiently low to avoid ammonia inhibition problems. The systems may be operated under mesophilic or thermophilic conditions.

4 Claims, 2 Drawing Sheets

OTHER PUBLICATIONS

Kayhanian, Ammonia Inhibition in High–Solids Biogasification: An Overview and Practical Solutions, Env. Tech., vol. 20, pp. 35–65, 11/98.

Guerrero et al., Anaerobic Hydrolysis and Acidogenesis of Wastewaters from Food Industries with High Content of Organic Solids and Protein, Wat. Res., vol. 33, No. 15, pp. 3281–3290, 01/99.

Zoutberg et al., Anaerobic Treatment of Potato Processing Wastewater, Wat. Sci. Tech. 19990000, pp. 297–303, 09/98.

* cited by examiner

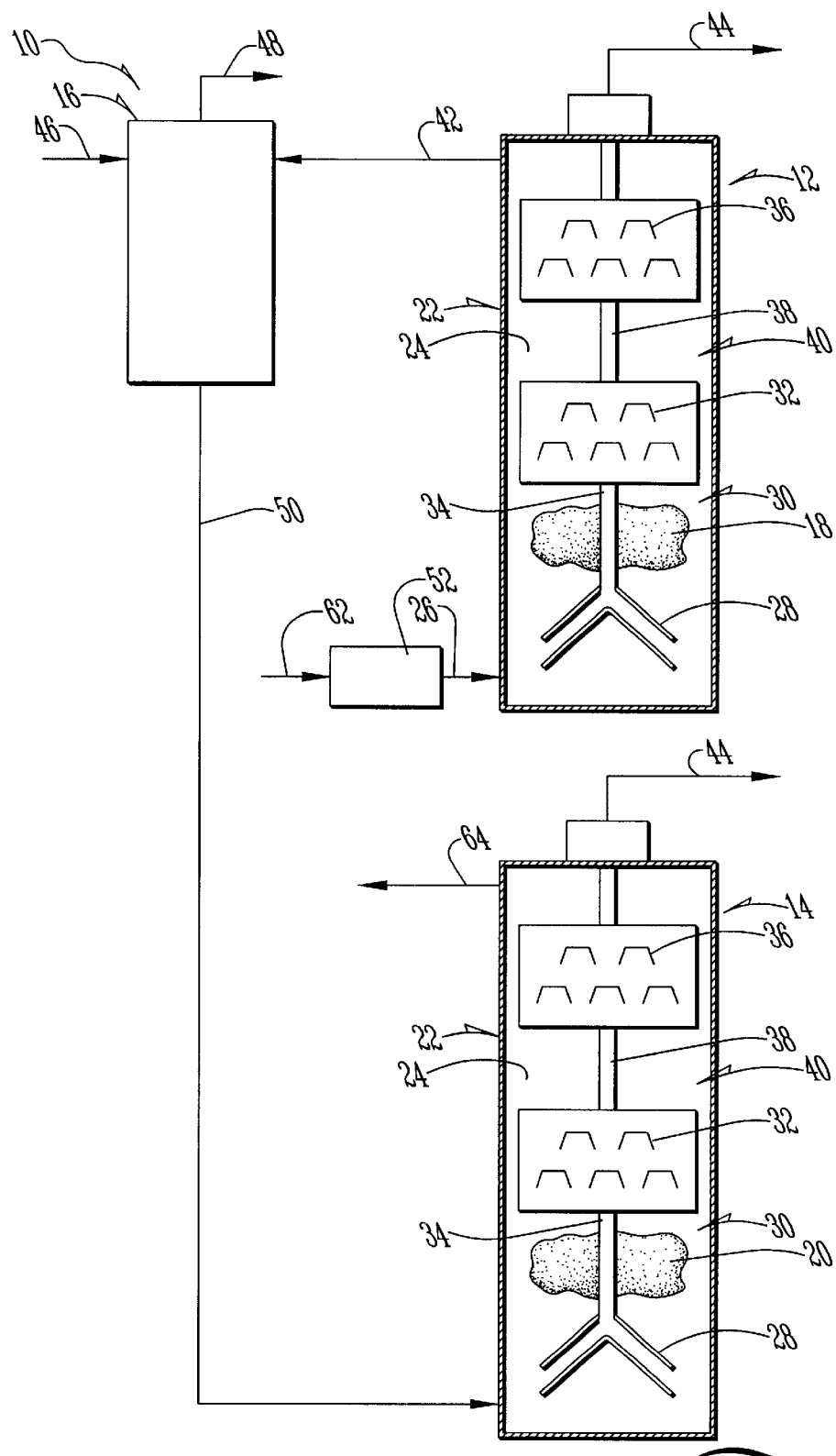

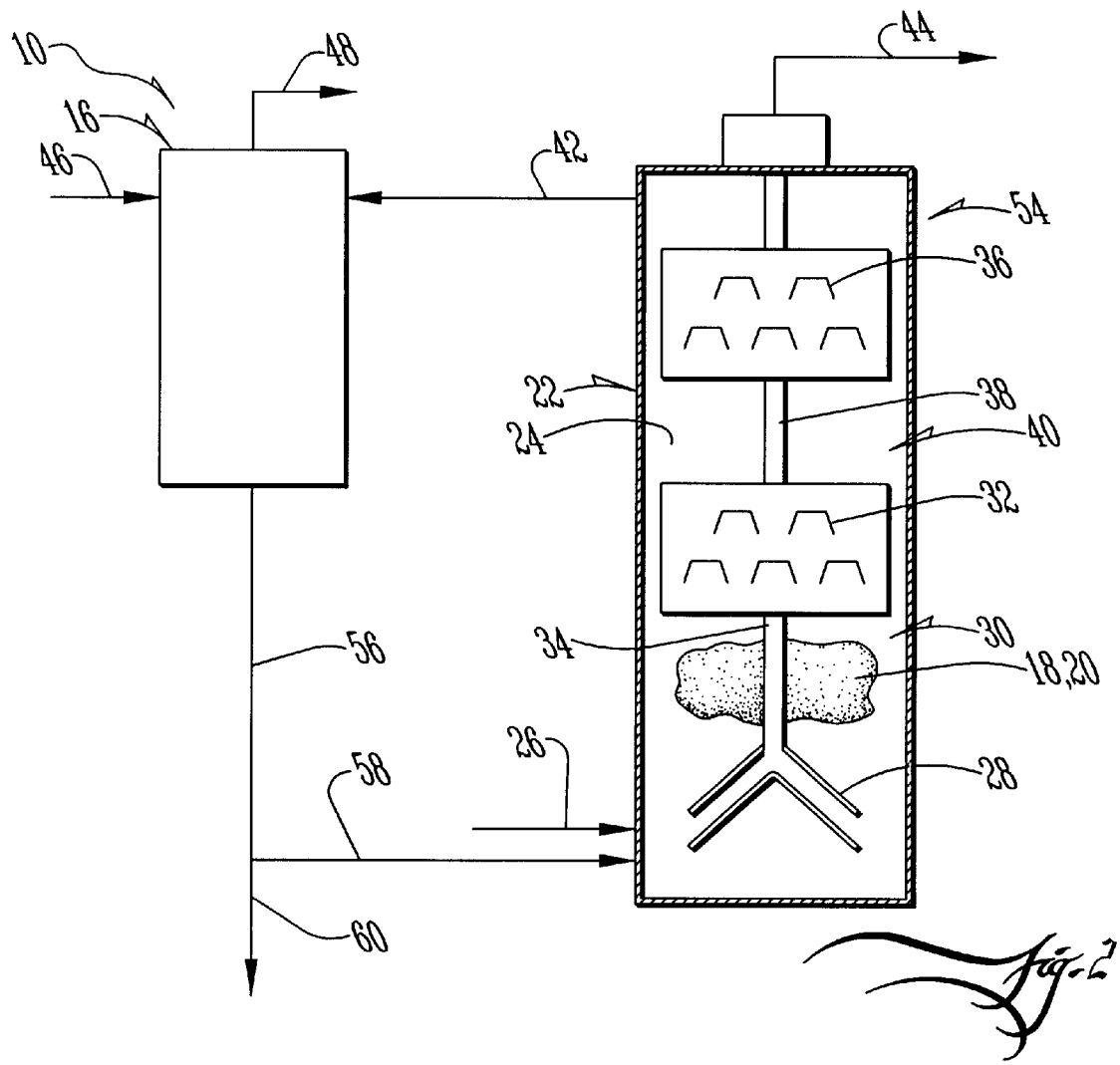

ENHANCED BIOGAS PRODUCTION FROM NITROGEN BEARING FEED STOCKS

BACKGROUND OF THE INVENTION

This invention relates to the anaerobic treatment of feed stocks to generate biogas, and more particularly to the anaerobic treatment of nitrogen containing feed stocks to generate a biogas.

Over the past several decades, extensive scientific and engineering work has been conducted on the biogasification of waste materials. The fundamental technique relies on the anaerobic digestion or fermentation process. Anaerobic digestion of biomass materials proceeds in three distinct and sequential pathways. These pathways are hydrolysis, acetogenesis and methanogenesis. The anaerobic microorganisms that conduct the first two steps, the hydrolyzers and acetogens, break the complex biomass molecules down into small chain molecules. Proteins are hydrolyzed into proteoses, peptones and polypeptides. These compounds are further broken down into ammonia and small chain fatty acids such as acetic acid, butyric acid, propionic acid,. and lactic acid. The anaerobic microorganisms that perform the hydrolysis and acetogenesis functions are highly resistant to ammonia. Anaerobic fermentation of high nitrogen wastes using these microorganisms have produced digested streams containing in excess of 10,000 ppm ammonia. However, the anaerobic microorganisms responsible for methanogenesis are inhibited by ammonia. Methanogenesic anaerobic bacteria cease to function effectively at ammonia concentrations equal to or greater than approximately 1,200 ppm ammonia. (Kayhanian, M., *Environmental Technology*, Vol. 20, PP 355–365. 1999)

Technologies such as the Upflow Anaerobic Sludge Blanket (UASB) reactor and the Extended Granular Sludge Bed (EGSB) reactor offer advantages in the anaerobic fermentation or digestion of wastewater or other feed stocks. These reactors allow for higher treatment rates using smaller vessels, thereby reducing capital costs. These reactors also provide for improved odor control. Still, problems associated with ammonia inhibition have made these reactors relatively unstable and difficult to operate when using feed stocks containing relatively high concentrations of nitrogen. To mitigate these problems, it has been proposed to control the carbon to nitrogen (C/N) ratio of the feed stock and to dilute the reactors with water in cases of sudden, large ammonia overloads. These proposals still suffer from a number of disadvantages. For example, adjusting the ammonia concentration in a reactor by adjusting the C/N ratio of the feed stock is a slow process, it can be difficult to accurately determine the C/N ratio, and adjusting the C/N ratio may prove to be insufficient to handle feed stocks that are prone to generate relatively high ammonia concentrations during anaerobic digestion. Dilution of a reactor with water also has a number of disadvantages. For example, diluting the reactor with water may seriously decrease the reactor's biogas production for extended periods of time and will typically lead to increased dewatering costs. Dilution of an existing feed stock increases the required reactor volume for digestion of that feed stock. An existing reactor would have a decreased capacity for treating a given feed stock if that feed stock were diluted.

SUMMARY OF THE INVENTION

It is therefore an object of the present invention to provide a stable system for treating nitrogen containing biomass materials to generate a biogas.

It is a further object of the present invention to provide a system of the above type that provides for separation of the anaerobic digestion process so that methanogenesis takes place in a separate reactor or other receptacle.

It is a still further object of the present invention to provide a system of the above type in which ammonia removal prior to methanogenesis keeps ammonia levels sufficiently low to avoid ammonia inhibition problems.

It is a still further-object of the present invention to provide a system of the above type in which the system is operated under mesophilic, conditions.

It is a still further object of the present invention to provide a system of the above type in which the system is operated under thermophilic conditions.

It is a still further object of the present invention to provide an alternate embodiment of a system of the above type in which effluent from a reactor is treated for ammonia removal and recycled to the reactor at a rate sufficient to keep ammonia levels within the reactor sufficiently low to avoid ammonia inhibition problems.

Toward the fulfillment of these and other objects and advantages, the system of the present invention comprises a first anaerobic digester, an ammonia recovery vessel, and a second anaerobic digester. Microorganisms within the first anaerobic digester are primarily hydrolyzers and acetogens, and microorganisms within the second anaerobic digester are primarily methanogens. A nitrogen containing feed stock is passed to the first digester in which the feed stock is treated to accomplish hydrolysis and acetogenesis. An effluent stream from the first digester is passed to the ammonia recovery vessel in which ammonia is removed to generate a low ammonia effluent stream. The low ammonia effluent stream is then passed to the second digester in which it is treated to accomplish me thanogenesis, thereby generating a biogas. In an alternate embodiment, a single anaerobic digester is used, an effluent stream is removed from the reactor, treated for ammonia removal, and recycled to the digester at a rate sufficient to keep ammonia levels within the digester sufficiently low to avoid ammonia inhibition problems. The systems may be operated under mesophilic or thermophilic conditions.

BRIEF DESCRIPTION OF THE DRAWINGS

The above brief description, as well as further objects, features and advantages of the present invention will be more fully appreciated by reference to the following detailed description of the presently preferred but nonetheless illustrative embodiments in accordance with the present invention when taken in conjunction with the accompanying drawings, wherein:

FIG. 1 is a schematic diagram of a system of the present invention; and

FIG. 2 is a schematic diagram of an alternate embodiment of the present invention.

DETAILED DESCRIPTION OF THE PREFERRED EMBODIMENT

Referring to FIG. 1, the reference numeral 10 refers in general to a system of the present invention, comprising two anaerobic digesters or reactors 12 and 14 and an ammonia removal or recovery vessel 16. Anaerobic microorganisms comprising primarily hydrolzyers and acetogens 18 are present in the first reactor 12, and anaerobic microorganisms comprising primarily methanogens 20 are present in the second reactor 14.

The structure of the reactors 12 and 14 is similar, so only one will be described in detail. The reactor 12 features an enclosure 22 defining a chamber 24. A conduit 26 is provided near the bottom of the enclosure 22 for providing a nitrogen containing feed stock. Baffles 28 near the bottom help to distribute the feed stock. Above the baffles 28 is a fluidized bed area 30 having the anaerobic microorganisms comprising primarily hydrolyzers and acetogens 18. A second set of baffles 32 is provided at an intermediate point above the fluidized bed area 30 to serve as a first settler area. A downer conduit 34 extends between the second set of baffles 32 and the lower first set of baffles 28. A third set of baffles 36 is provided near an upper portion of the chamber 24 to serve as a second settler area. A gas riser conduit 38 extends between the second and third sets of baffles 32 and 36. The area between the second and third sets of baffles 32 and 36 comprises a polishing area 40. An effluent conduit 42 exits the enclosure 22 above the third set of baffles 36, and a gas removal conduit 44 exits from a top portion of the enclosure 22.

The conduit 42 connects the first reactor 12 to an ammonia recovery or removal vessel or receptacle 16. Any of a wide variety of ammonia recovery or removal processes and vessels may be used. Ammonia recovery and removal processes such as the Ammonia Recovery Process, (ARP), adsorption, air stripping, steam stripping, and combinations of such processes are well known in the art and will not be discussed in detail. Conduits 46 and 48 may provide for the introduction of reactants, such as $H_2SO_4$, and for the recovery or removal of ammonia, such as in the form of $(NH_4)_2SO_4$. An effluent conduit 50 connects the ammonia recovery vessel 16 to the second reactor 14, providing a feed stock near the bottom of the chamber 24. The structure of the second reactor 14 is similar to the structure of the first reactor 12 and will not be discussed in detail. In the fluidized bed area 30 of the second reactor 14, the anaerobic microorganisms are comprised primarily of methanogens 20.

As also shown in FIG. 1, a receptacle or vessel 52 may be provided for hydrothermal liquefaction, rendering, or a similar process upstream of the first reactor 12.

Referring to FIG. 2, an alternate embodiment is disclosed in which effluent recycle with ammonia removal is used in connection with a single anaerobic digestion reactor 54. The structure of the reactor 54 is similar to the structure of the reactors 12 and 14 discussed above and will not be discussed in more detail. In the alternate embodiment, a conduit 56 exits the ammonia recovery vessel 16, and conduits 58 and 60 allow for a portion of the effluent from the reactor to be recycled to the reactor 54 after being treated for ammonia removal or recovery and a portion of that effluent to be passed for disposal or further processing. The conduit 58 connects with feed conduit 26 or enters the enclosure 22 near the bottom of the chamber 24.

Returning to FIG. 1, in operation, a nitrogen containing feed stock or waste stream containing biomass materials is fed via conduit 62 to a first receptacle or vessel 52 for hydrothermal liquefaction, rendering, or a similar process. The feed stock may be a high chemical oxygen demand (COD), high nitrogen wastewater, such as from a concentrated animal feeding operation (CAFO). For the present system 10, it is preferred to use a feed stock stream comprising a high strength wastewater containing a low-level of suspended solids. Such a stream is produced by the hydrothermal liquefaction of biomass materials such as sewage sludge. Such streams contain a high Total Kjeldahl Nitrogen (TKN) and ammonia nitrogen load as well as a high biological oxygen demand. The benefit from hydrothermal liquefaction is that it dissolves biomass solids by hydrolyzing hair, cellulose, and cellular proteins into water-soluble saccharides, proteoses, peptones and peptides. These water-soluble and partially water-soluble materials are in a form that is much more available to anaerobic microorganisms. After treatment for hydrothermal liquefaction, the stream passes via conduit 26 to a lower portion of the first reactor 12.

In the first reactor 12, the hydrolyzers and acetogens 18 are reacted with the feed stock to accomplish hydrolysis and acetogenesis. The hydrolyzers and acetogens 18 are highly resistant to ammonia, so these two stages of anaerobic fermentation or digestion may be accomplished without ammonia inhibition problems even for feed stocks with relatively high nitrogen contents. For example, the concentration of ammonia within the first reactor 12 will often reach or exceed 1,200 ppm, will sometimes reach or exceed 5,000 ppm, and will occasionally reach or exceed 10,000 ppm, all without creating ammonia inhibition problems for the hydrolysis and acetogenesis functions of the reactor 12. The reaction is preferably accomplished under mesophilic conditions and more preferably under thermophilic conditions. Mesophilic digestion is accomplished at a temperature that is preferably substantially within a range of from approximately 30° C. to approximately 45° C., and that is more preferably approximately 37° C. Thermophilic digestion is accomplished at a temperature that is preferably substantially within a range of from approximately 45° C. to approximately 60° C., and that is more preferably approximately 55° C. This elevated temperature is beneficial because it aids in the removal of ammonia by all three of the processes mentioned above. In addition, thermophilic reactions are typically faster than mesophilic processes conducted at approximately 30°–45° C. An advantage of processing high strength wastewater in a thermophilic anaerobic digester is that the residence time and size of the reactor is smaller for a given throughput. An advantage of processing high strength wastewater in a mesophilic anaerobic digester is that the feed stock does not have to be heated to as high a temperature as needed in a thermophilic reactor.

A relatively small amount of biogas is produced in the first reactor 12 and exits from conduit 44 at the top of the enclosure 22. The first reactor 12 preferably generates less than approximately 30% of the total amount of biogas generated by the system 10 and more preferably generates less than approximately 10% of the total amount of biogas generated by the system 10.

An acetate and ammonia rich effluent passes from an upper portion of the first reactor 12 to the ammonia recovery vessel 16 via conduit 42. In the ammonia recovery vessel 16, ammonia is recovered or removed by any known ammonia recovery or removal process. Conduits 46 and 48 may provide for the introduction of reactants, such as $H_2SO_4$, and for the recovery or removal of ammonia, such as in the form of $(NH_4)_2SO_4$. Other reactants such as NaOH may be used to adjust the pH of the low ammonia, acetate rich stream to improve its suitability for methanogen digestion. Conduit 50 passes a low ammonia, acetate rich effluent stream from the ammonia recovery vessel 16 to the second reactor 14. The ammonia content in the low ammonia effluent stream is preferably below approximately 1,200 ppm and is more preferably below approximately 600 ppm.

In the second reactor 14, the methanogens 20 are reacted with the low ammonia, acetate rich feed stream to accomplish methanogenesis. The methanogens 20, or anaerobic microorganisms responsible for methanogenesis, are inhibited by ammonia. Methanogens 20 cease to function effectively at ammonia concentrations equal to or greater than approximately 1,200 ppm ammonia. Accordingly, sufficient ammonia is removed during the ammonia recovery stage to maintain the ammonia concentration within the second reactor 14 at a level that is preferably below approximately 1,200 ppm and more preferably below approximately 600 ppm. The anaerobic methanogenesis reaction is preferably accomplished under mesophilic conditions and more preferably under thermophilic conditions. Mesophilic digestion is accomplished at a temperature that is preferably substantially within a range of from approximately 30° C. to approximately 45° C., and that is more preferably approximately 37° C. Thermophilic digestion is accomplished at a temperature that is preferably substantially within a range of from approximately 45° C. to approximately 60° C., and that is more preferably approximately 55° C. This elevated temperature is beneficial because it aids in the removal of ammonia by all three of the processes mentioned above. In addition, thermophilic reactions are typically faster than mesophilic processes conducted at approximately 30°–45° C.

A relatively large amount of biogas is produced in the second reactor 14 and exits from the top of the enclosure 22 via conduit 44. The second reactor 14 preferably generates greater than approximately 70% of the total amount of biogas generated by the system 10 and more preferably generates greater than approximately 90% of the total amount of biogas generated by the system 10. A low COD, low ammonia effluent is discharged from an upper portion of the second reactor 14 via conduit 64 and may be passed to a wastewater treatment process or facility.

In this manner, the anaerobic fermentation is conducted in two separate stages. The hydrolysis and/or acetogenesis portion of the fermentation is conducted in a first stage, the ammonia is then removed from the acetate rich wastewater, and methanogenesis is conducted in the second stage of the anaerobic fermentation.; This allows for superior biogas production levels while avoiding problems associated with ammonia inhibition.

In the alternate embodiment depicted in FIG. 2, a reactor or upflow anaerobic digester 54 such as an EGSB is provided with an ammonia removal vessel 16 and a recycle stream 58. A nitrogen containing feed stock or waste stream containing biomass materials may be fed to a first receptacle or vessel (not shown in FIG. 2) for hydrothermal liquefaction, rendering, or a similar process. The feed stock may be a high COD, high nitrogen wastewater, such as from a CAFO. After treatment for hydrothermal liquefaction, the stream passes via conduit 26 to a lower portion of the reactor 54.

In the reactor 54, the hydrolyzers, acetogens, and methanogens 18 and 20 are fed with the feed stock to accomplish the hydrolysis, acetogenesis, and methanogenesis reactions. The reaction is preferably accomplished under mesophilic conditions and more preferably under thermophilic conditions. Mesophilic digestion is accomplished at a temperature that is preferably substantially within a range of from approximately 30° C. to approximately 45° C., and that is more preferably approximately 37° C. Thermophilic digestion is accomplished at a temperature that is preferably substantially within a range of from approximately 45° C. to approximately 60° C., and that is more preferably approximately 55° C.

Biogas is produced in the reactor 54 and exits from the top of the enclosure 22 via conduit 44. An effluent passes from an upper portion of the reactor to the ammonia recovery vessel 16 via conduit 42. In the ammonia recovery vessel 16, ammonia is recovered or removed by any known ammonia recovery or removal process. Conduits 46 and 48 may provide for the introduction of reactants, such as $H_2SO_4$, and for the recovery of ammonia, such as in the form of $(NH_4)_2SO_4$. Other reactants such as NaOH may be used to adjust the pH of the low ammonia, acetate rich stream to improve its suitability for methanogen digestion. The low ammonia effluent exits the ammonia recovery vessel 16 via conduit 56, and a portion of the low COD, low ammonia stream may be passed via conduit 60 to a wastewater treatment process or facility. Conduit 58 passes a portion of the low ammonia effluent stream from the ammonia recovery vessel 16 to the reactor 54 to dilute the feed stock so that ammonia levels in the reactor 54 remain below inhibition levels. The ammonia content in the low ammonia effluent stream is preferably below approximately 1,200 ppm, is more preferably below approximately 600 ppm, and is most preferably below approximately 300 ppm. Similarly, because methanogens 20 are in the reactor 54, it is important to maintain a relatively low ammonia concentration within the reactor 54. A sufficient degree of ammonia removal is achieved in the ammonia recovery vessel 16, and a sufficient portion of the low ammonia; effluent stream is recycled to the reactor 54 to maintain ammonia concentrations within the reactor 54 at a level that will avoid ammonia inhibition problems. The ammonia concentration within the reactor 54 is preferably maintained below approximately 1,200 ppm and is more preferably maintained below approximately 600 ppm.

The configuration depicted in FIG. 2 may be used when the feed material is highly concentrated or contains toxic materials. As discussed in more detail above, in this embodiment, ammonia is continuously removed from a recycle stream, which enables the reactor 54 to operate at a sufficiently low ammonia concentration such that the methanogens 20, or methanogenic bacteria, are not inhibited. Similar to the first embodiment, the ammonia is removed by use of an Ammonia Recovery Process, ARP, adsorption, air stripping, or steam stripping, or any of a wide variety of ammonia removal or recovery techniques or some combination thereof.

The ammonia inhibition of methanogenic anaerobic bacteria by ammonia is a limitation on the production of biogas from nitrogen containing feed stocks. It will be appreciated that the present system 10 may be incorporated into or used in connection with a wide variety of anaerobic digestion systems and technologies, such as UASB and EGSB systems, to improve biogas production.

Other modifications, changes and substitutions are intended in the foregoing, and in some instances, some features of the invention will be employed without a corresponding use of other features. For example, the system 10 may be used with or without wastewater pretreatment such as hydrothermal liquefaction, rendering or the like. Also, the feed stock may come from any number of different sources, including but not limited to CAFOs, food processing plants, and wastewater treatment facilities. Further, the recycle feature may be used in connection with either embodiment. Further still, it is understood that the reactor receptacles or vessels 12, 14, 16, and 54 may take any number of shapes, sizes, and configurations and need not have the structure described in connection with the preferred embodiments. Further, it is understood that the various reactions may take place under different conditions, using different styles or types of reactors. For example, it is understood that hydrolysis and acetogenesis may be accomplished under thermophilic conditions while methanogenesis may be accomplished under mesophilic conditions, and vice versa. Similarly, it is understood that hydrolysis and acetogenesis may be accomplished using a reactor such as an UASB reactor while methanogenesis may be accomplished using a different style reactor such as an EGSB reactor, or vice versa. It is also understood that all quantitative information given is by way of example only and is not intended to limit the scope of the present invention. Accordingly, it is appropriate that the appended claims be construed broadly and in a manner consistent with the scope of the invention.

What is claimed is:

1. A method, comprising:
   (1) passing a nitrogen containing feed stock to a first receptacle;
   (2) treating said feed stock in said first receptacle to accomplish hydrolysis, acetogenesis, and methanogenesis;
   (3) removing a biogas generated in said first receptacle;
   (4) passing an effluent from said first receptacle to a second receptacle;
   (5) treating said effluent in said second receptacle to remove ammonia from said effluent to leave a low ammonia effluent; and
   (6) passing an amount of said low ammonia effluent to said first receptacle.

2. The method of claim 1, wherein step (6) comprises:
   passing an amount of said low ammonia effluent to said first receptacle, said amount being sufficient to maintain an ammonia concentration within said first receptacle of less than approximately 1,200 ppm.

3. The method of claim 2, further comprising:
   maintaining contents within said first receptacle at a temperature that is substantially within a range of from approximately 45° C. to approximately 60° C.

4. The method of claim 1, wherein step (6) comprises:
   passing an amount of said low ammonia effluent to said first receptacle, said amount being sufficient to maintain an ammonia concentration within said first receptacle of less than approximately 600 ppm.

* * * * *